United States Patent
Ozog, III et al.

(10) Patent No.: US 6,358,540 B1
(45) Date of Patent: Mar. 19, 2002

(54) HERBAL COMPOSITION FOR TREATMENT OF TINNITUS

(76) Inventors: Stanley T. Ozog, III, 4651 Pico St., #111, San Diego, CA (US) 92109; Delmar S. Neville, II, 1300 Bernita Rd., El Cajon, CA (US) 92020

( * ) Notice: Subject to any disclaimer, the term of this patent is extended or adjusted under 35 U.S.C. 154(b) by 0 days.

(21) Appl. No.: 09/708,218

(22) Filed: Nov. 7, 2000

(51) Int. Cl.⁷ .............................................. A61K 35/78
(52) U.S. Cl. .................. 424/725; 424/739; 424/741; 424/756; 424/757; 424/773; 424/776; 424/777; 424/778; 424/779
(58) Field of Search .................... 424/725, 739, 424/741, 756, 757, 773, 776, 777, 778, 779

(56) References Cited

U.S. PATENT DOCUMENTS 5,834,000 A * 11/1998 Yng-Wong

OTHER PUBLICATIONS

Bensky and Gamble. Chinese Herbal Medice: Materia Medica, Revised Edition. (1993), Seattle, Washington, Eastland Press, Inc. pp. 35–38.*
Derwent abstract of DE 3626128 A (Feb. 1998).*
Derwent abstract of CN 1267524 A (Sep. 2000).*
Derwent abstract of JP 06256203 A (Sep. 1994).*

* cited by examiner

Primary Examiner—Leon B. Lankford, Jr.
Assistant Examiner—Susan D. Coe
(74) Attorney, Agent, or Firm—John R. Ross; John R. Ross, III

(57) ABSTRACT

A method for treating tinnitus comprising the step of administering to a subject requiring such treatment a therapeutically effective amount of an herbal composition comprising Radix Puerariae, Radix Platycodi Grandiflori, Radix Angelicae Dahuricae, Semen Coicis Lachryma-jobi, Rhizoma Zigiberis Officinalis Recens, Radix Ligustici Chuanxiong, Radix Paeoniae Lactiflorae, Folium Perillae Frutescentis, Flos Magnoliae, Herba cum Radice Asari, Ramulus Cinnamomi Cassiae, Radix Scutellariae Baicalensis, and Radix Glycyrrhizae Uralensis.

3 Claims, 1 Drawing Sheet

| Patient No. | Sex | Age (years) | Occupation | Assumed Cause of Ringing | Years Suffering with Tinnitus | Results | Approximate length of time required for ringing to significantly diminish. | Approximate length of time for ringing to return after stopping intake of herbal composition. |
|---|---|---|---|---|---|---|---|---|
| Patient 1 | Male | 55 | Business Man | Exposure to loud noise | 10 | Ringing Drastically Reduced | 4 days | 2 days |
| Patient 2 | Male | 53 | Retired Construction Worker | Exposure to loud noise | 25 | Ringing Drastically Reduced | 2 days | 1 day |
| Patient 3 | Male | 38 | Retired Automotive Technician | Exposure to loud noise | 5 | Ringing Drastically Reduced | 2 days | 2 days |
| Patient 4 | Male | 50 | Musician | Exposure to loud music | 2 | Ringing Drastically Reduced | 1 day | 1 day |
| Patient 5 | Male | 55 | Businessman | Exposure to loud noise | 10 (intermittent ringing) | Ringing Drastically Reduced | 1 day | 2 days |
| Patient 6 | Male | 59 | Retired Shipyard Worker | Exposure to loud noise | 10 | Ringing Drastically Reduced | 2 days | 2 days |
| Patient 7 | Female | 65 | Homemaker | Exposure to loud noise | 20 | Ringing Drastically Reduced | 1 week | 3 days |

FIG. 1

HERBAL COMPOSITION FOR TREATMENT OF TINNITUS

This invention relates to new medicinal compositions and methods for treating ear disorders, in particular the treatment of tinnitus.

BACKGROUND OF THE INVENTION

Tinnitus is a hearing condition that effects a significant portion of the population and is characterized by the sufferer hearing an unpleasant ringing sensation. There are numerous sources available that describe tinnitus, its causes and known treatments. One such source is the OnHealth Network Company website www.onhealth.webmd.com. The OnHealth Network Company is a leading Internet health information and services resource. OnHealth's website states:

Tinnitus, or ringing in the ears, is the sensation of hearing ringing, buzzing, hissing, chirping, whistling or other sounds. The noise can be intermittent or continuous, and can vary in loudness. It is often worse when background noise is low, so you may be most aware of it at night when you're trying to fall asleep in a quiet room. In rare cases, the sound beats in sync with your heart. Tinnitus is very common, affecting an estimated 50 million adults in the United States. For most people the condition is merely an annoyance. In severe cases, however, tinnitus can cause people to have difficulty concentrating and sleeping. It may eventually interfere with work and personal relationships, resulting in psychological distress. About 12 million people seek medical help for severe tinnitus every year.

A wide variety of conditions and illnesses can lead to tinnitus. Blockages of the ear due to a buildup of wax, an infection, or rarely, a tumor of the auditory nerve can cause the unwanted sounds, as can a perforated eardrum. But perhaps the most common source of chronic tinnitus is prolonged exposure to loud sounds. The noise causes permanent damage to the sound-sensitive cells of the cochlea, a spiral-shaped organ in the inner ear. Carpenters, pilots, rock musicians and street-repair workers are among those whose jobs put them at risk, as are people who work with chain saws, guns or other loud devices or who repeatedly listen to loud music. A single exposure to a sudden extremely loud noise can also cause tinnitus.

Certain drugs—most notably aspirin, several types of antibiotics and quinine medications—can contribute to the condition as well. In fact, tinnitus is cited as a potential side effect for about 200 prescription and nonprescription drugs. The natural process of aging can result in a deterioration of the cochlea or other parts of the ear and lead to tinnitus.

Tinnitus is also associated with Meniere's disease, a disorder of the inner ear, and otosclerosis, a degenerative disease of the small bones in the middle ear. Other medical conditions that can cause ringing in the ears include high blood pressure, allergies, anemia and an underactive thyroid.

Tinnitus can also be a symptom of a disorder of the neck or jaw, such as temporomandibular joint (TMJ) syndrome. For reasons not yet entirely clear to researchers, stress seems to worsen tinnitus.

Known methods of treating Tinnitus include: 1) cleaning the ear with a cotton-tipped probe, 2) utilizing ear drops containing hydrocortisone, 3) surgery if otosclerosis or a tumor is diagnosed, 4) dental work, 5) drug treatment utilizing the drug LIDOCAINE (LIDOCAINE is a medication for the treatment of certain types of abnormal heart rhythms), 6) utilizing a hearing aid, 7) utilizing a tinnitus masker (a tinnitus masker is a device that resembles a hearing aid and it plays a sound that is more pleasant than the noise produced by the tinnitus), 8) utilizing a tinnitus instrument (a tinnitus instrument is a device that is a combination of a hearing aid and a tinnitus masker), and 9) utilizing a auditory habituation (a auditory habituation is where the tinnitus sufferer wears a device that emits a white noise that is quieter than the tinnitus sound; the brain learns to ignore, or habituate to the tinnitus sound).

Herbal Remedies

It is known in the prior art that it is possible to utilize various herbs and herbal compositions to treat tinnitus. A listing of some of the herbs can be found in *Chinese Herbal Medicine: Materia Medica, Revised Edition*, compiled and translated by Dan Bensky and Andrew Gamble. A summary of some known herbs and their therapeutic properties is listed below in Table 1:

TABLE 1

| Herb Pharmaceutical Name | Some Known Uses of the Herb |
| --- | --- |
| Radix Puerariae | Treats symptoms of hypertension: this herb has recently been used to treat the headache, dissiness, tinnitus, or paresthesias that can accompany hypertension. |
| Radix Platycodi Grandiflori | Directs the effect of other herbs to the upper regions of the body. |
| Radix Angelicae Dahuricae | Alleviates pain and opens up nasal passages for sinus congestion. |
| Semen Coicis Lachryma-jobi | Removes excess moisture, promotes sinus drainage; strengthens the spleen. |
| Rhizoma Zingiberis Officinalis Recens | Reduces the toxicity of other herbs. |
| Radix Ligustici Chuanxiong | Alleviates pain, during headaches it moves the qi upward and alleviates pain. |
| Radix Paeoniae Lactiflorae | Nourishes the blood and preserves the yin. |
| Folium Perillae Frutescentis | Promotes the movement of qi. |
| Flos Magnoliae | It can be used for any nasal or sinus condition, depending on the other herbs in the prescription. |
| Herba cum Radice Asari | Alleviates pain. Disperses an unblocks the qi of the nasal orifices. |
| Radix Scutellariae Baicalensis | For symptoms such as headache and irritability. |
| Ramulus Cinnamomi Cassiae | Unblocks the yang and transforms the qi. |
| Radix Glycyrrhizae Uralensis | Moderates and harmonizes the characteristics of other herbs. Also used as an antidote for a variety of toxic substances, both internally and topically. |

Likewise, a listing of herbal compositions can be found in *Chinese Herbal Medicine: Formulas and Strategies*, compiled and translated by Dan Bensky and Randall Barolet.

Although it is known to treat tinnitus with certain herbs or with a combination of certain herbs, there are problems with known herbal and herbal combination treatments for tinnitus. The known herbal treatments tend to have only limited effectiveness and they tend to cause unpleasant side effects in for a significant amount of patients. These side effects include diarrhea, sleeplessness, irritability, and nausea.

What is needed is a better method for treating tinnitus.

SUMMARY OF THE INVENTION

The present invention provides a method for treating tinnitus comprising the step of administering to a subject requiring such treatment a therapeutically effective amount of an herbal composition comprising Radix Puerariae, Radix Platycodi Grandiflori, Radix Angelicae Dahuricae, Semen Coicis Lachryma-jobi, Rhizoma Zigiberis Officinalis Recens, Radix Ligustici Chuanxiong, Radix Paeoniae Lactiflorae, Folium Perillae Frutescentis, Flos Magnoliae, Herba cum Radice Asari, Ramulus Cinnamomi Cassiae, Radix Scutellariae Baicalensis, and Radix Glycyrrhizae Uralensis.

BRIEF DESCRIPTION OF THE DRAWINGS

FIG. 1 shows a table summarizing the results of a preferred embodiment of the present invention.

DETAILED DESCRIPTION OF A PREFERRED EMBODIMENT

In a first preferred embodiment, the composition of the present invention includes the herbs Radix Puerariae, Radix Platycodi Grandiflori, Radix Angelicae Dahuricae, Semen Coicis Lachryma-jobi, Rhizoma Zigiberis Officinalis Recens, Radix Ligustici Chuanxiong, Radix Paeoniae Lactiflorae, Folium Perillae Frutescentis, Flos Magnoliae, Herba cum Radice Asari, Ramulus Cinnamomi Cassiae, Radix Scutellariae Baicalensis, and Radix Glycyrrhizae Uralensis. The herbs may each be included in concentration of from approximately 1% to 30% of the total weight of the herbal composition.

In a second preferred embodiment, the composition of the present invention includes each herb combined within the proportions given in Table 2.

TABLE 2

| Chinese Name | Pharmaceutical Name | Percentage of Herb |
| --- | --- | --- |
| Ge Gen | Radix Puerariae | 10–20% |
| Jie Geng | Radix Platycodi Grandiflori | 8–18% |
| Bai Zhi | Radix Angelicae Dahuricae | 3–12% |
| YI YI Ren | Semen Coicis Lachryma-jobi | 3–12% |
| Sheng Jiang | Rhizoma Zigiberis Officinalis Recens | 3–12% |
| Chuan Xiong | Radix Ligustici Chuanxiong | 3–12% |
| Bai Shao | Radix Paeoniae Lactiflorae | 3–12% |
| Zi Su Ye | Folium Perillae Frutescentis | 2–10% |
| Xin Yi Hua | Flos Magnoliae | 2–10% |
| Xi Xin | Herba cum Radice Asari | 2–10% |
| Gui Zhi | Ramulus Cinnamomi Cassiae | 2–10% |
| Huang Qin | Radix Scutellariae Baicalensis | 2–10% |
| Gan Cao | Radix Glycyrrhizae Uralensis | 2–10% |

Although the administration of the compositions described in the first preferred embodiment and the second preferred embodiment would be successful in the treatment of tinnitus, exemplary results were obtained utilizing the third preferred embodiment, described below in Table 3.

TABLE 3

| Chinese Name | Pharmaceutical Name | Percentage of Herb |
| --- | --- | --- |
| Ge Gen | Radix Puerariae | 15% |
| Jie Geng | Radix Platycodi Grandiflori | 13% |
| Bai Zhi | Radix Angelicae Dahuricae | 8% |
| YI YI Ren | Semen Coicis Lachryma-jobi | 8% |
| Sheng Jiang | Rhizoma Zigiberis Officinalis Recens | 8% |
| Chuan Xiong | Radix Ligustici Chuanxiong | 8% |
| Bai Shao | Radix Paeoniae Lactiflorae | 8% |
| Zi Su Ye | Folium Perillae Frutescentis | 6% |
| Xin Yi Hua | Flos Magnoliae | 6% |
| Xi Xin | Herba cum Radice Asari | 5% |
| Gui Zhi | Ramulus Cinnamomi Cassiae | 5% |
| Huang Qin | Radix Scutellariae Baicalensis | 5% |
| Gan Cao | Radix Glycyrrhizae Uralensis | 5% |

Test Study

Herbs and Preparation of Formulations

The components of the standard herbal formulation used in this study are listed in Table 3. All herbs were first dried, and then ground so that they were in powdered form, and then encapsulated before being administered to patients. If sufficiently dry, the herbs were powdered using a grinder or similar device. If the moisture content of the herbs was high, the herbs were baked before being powdered. The powder is then weighed and amounts of 500 mg are encapsulated in digestible capsules.

The herbs may also be formulated by one of the following methods:

(a) concentrating either a water or an organic solvent (eg. alcohol) extract of each herb and then combining the extracts;

(b) all the raw herbs can be boiled together and then concentrated by spray drying or other known methods into a dry granulated formulation.

In both cases the extracts are then concentrated before or after combining and may be processed into tablets or capsules.

Patient Selection

Five patients with tinnitus volunteered to participate in a study to evaluate the effectiveness of the present invention. Each of the patients was an adult and was in otherwise good health. Each patient was free to withdraw from the study at any time. Each patient was a tinnitus sufferer who had previously been unable to achieve relief from the tinnitus. The description of the patients and the results of the study are summarized in the table shown in FIG. 1.

Herbal Preparation and Dosage

All patients took the same dose of one capsule twice per day. Each capsule was approximately 500 mg.

Results of the Study

As shown in FIG. 1, each of the patients participating in the study reported that their ear ringing was drastically reduced to a level that caused them no discomfort, irritation or anxiety. The amount of time it took for the present invention to provide relief is also shown in FIG. 1. Also, the patients reported that so long as they continued to take the recommended dosage of one capsule twice per day, the ear ringing continued to remain at the reduced manageable level.

Effect of Discontinuing Usage of the Present Invention

As stated above, all patients each enjoyed remarkable success in alleviating symptoms of tinnitus by usage of the present invention. All patients discontinued taking the present invention in order to ascertain whether the ear ringing would return. All patients reported that soon after discontinuation of the present invention, the unpleasant ear ringing returned to the same level it was at prior to starting the study. The amount of time it took for the ringing to return is shown in FIG. 1.

However, after the patients once again started taking the recommended dosage of the present invention the symptoms were again drastically reduced.

Conclusion

Based on the study outlined above, the conclusion is that by utilization of the present invention a tinnitus sufferer is likely to enjoy remarkable success in alleviating symptoms of tinnitus. It is preferable, that in order to continue to enjoy drastically reduced ear ringing, a tinnitus sufferer should take the present invention on a regular basis.

While the present invention has been described in relation to particular embodiments, persons skilled in the art will recognize that many potential variations are possible. For these reasons the scope of this invention is to be determined by the appended claims and their legal equivalents.

We claim:

1. A method for treating tinnitus comprising administering to a subject requiring such treatment a therapeutically effective amount of an herbal composition comprising Radix Puerariae, Radix Platycodi Grandiflori, Radix Angelicae Dahuricae, Semen Coicis Lachryma-jobi, Rhizoma Zingiberis Officinalis Recens, Radix Ligustici Chuanxiong, Radix Paeoniae Lactiflorae, Folium Perillae Frutescentis, Flos Magnoliae, Herba cum Radice Asari, Ramulus Cinnamomi Cassiae, Radix Scutellariae Baicalensis, and Radix Glycyrrhizae Uralensis.

2. The method as in claim 1, wherein the percentage of Radix Puerariae is about 10%–20%, the percentage of Radix Platycodi Grandiflori is about 8%–18%, the percentage of Radix Angelicae Dahuricae is about 3%–12%, the percentage of Semen Coicis Lachryma-jobi is about 3%–12%, the percentage of Rhizoma Zingiberis Officinalis Recens is about 3%–12%, the percentage of Radix Ligustici Chuanxiong is about 3%–12%, the percentage of Radix Paeoniae Lactiflorae is about 3%–12%, the percentage of Folium Perillae Frutescentis is about 2%–10%, the percentage of Flos Magnoliae is about 2%–10%, the percentage of Herba cum Radice Asari is about 2%–10%, the percentage of Ramulus Cinnamomi Cassiae is about 2%–10%, the percentage of Radix Scutellariae Baicalensis 2%–10%, and the percentage of Radix Glycyrrhizae Uralensis is about 2%–10%, wherein each ingredient is added in percentage by weight of the total composition.

3. The method as in claim 1, wherein the percentage of Radix Puerariae is about 15%, the percentage of Radix Platycodi Grandiflori is about 13%, the percentage of Radix Angelicae Dahuricae is about 8%, the percentage of Semen Coicis Lachryma-jobi is about 8%, the percentage of Rhizoma Zingiberis Officinalis Recens is about 8%, the percentage of Radix Ligustici Chuanxiong is about 8%, the percentage of Radix Paeoniae Lactiflorae is about 8%, the percentage of Folium Perillae Frutescentis is about 6%, the percentage of Flos Magnoliae is about 6%, the percentage of Herba cum Radice Asari is about 5% the percentage of Ramulus Cinnamomi Cassiae is about 5%, the percentage of Radix Scutellariae Baicalensis 5%, and the percentage of Radix Glycyrrhizae Uralensis is about 5%, wherein each ingredient is added in percentage by weight of the total composition.

* * * * *